(12) United States Patent
Schaff et al.

(10) Patent No.: US 9,244,065 B1
(45) Date of Patent: Jan. 26, 2016

(54) SYSTEMS, DEVICES, AND METHODS FOR AGGLUTINATION ASSAYS USING SEDIMENTATION

(75) Inventors: Ulrich Y. Schaff, Livermore, CA (US); Gregory J. Sommer, Livermore, CA (US); Anup K. Singh, Danville, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/423,073

(22) Filed: Mar. 16, 2012

(51) Int. Cl.
| | |
|---|---|
| G01N 33/543 | (2006.01) |
| G01N 33/537 | (2006.01) |
| B01D 21/26 | (2006.01) |
| B01L 3/00 | (2006.01) |
| G01N 33/538 | (2006.01) |

(52) U.S. Cl.
CPC .......... *G01N 33/537* (2013.01); *B01D 21/262* (2013.01); *B01L 3/5021* (2013.01); *G01N 33/538* (2013.01); *G01N 33/543* (2013.01); *G01N 33/54313* (2013.01); *G01N 33/54366* (2013.01); *B01L 2400/0409* (2013.01); *B01L 2400/0457* (2013.01)

(58) Field of Classification Search
CPC .......... G01N 33/543; G01N 33/54313; G01N 33/537; G01N 33/538; G01N 33/54366; B01D 21/26; B01D 21/262; B01D 21/00; B01D 43/00
USPC .............. 436/824, 518, 536, 538, 523, 528; 435/287.2, 7.1, 287.1, 7.92, 7.94, 969
See application file for complete search history.

(56) References Cited

U.S. PATENT DOCUMENTS

| | | | |
|---|---|---|---|
| 3,376,083 | A | 4/1968 | Everhardus |
| 3,555,284 | A | 1/1971 | Anderson |
| 3,744,974 | A | 7/1973 | Maddox |
| 3,844,341 | A | 10/1974 | Bimshas et al. |
| 4,125,375 | A | 11/1978 | Hunter |
| 4,156,570 | A | 5/1979 | Wardlaw |
| 4,164,690 | A | 8/1979 | Muller et al. |
| 4,282,464 | A | 8/1981 | Uzuka |
| 4,380,355 | A | 4/1983 | Beardmore |
| 4,554,071 | A | 11/1985 | Ruijten et al. |
| 4,656,143 | A | 4/1987 | Baker et al. |

(Continued)

FOREIGN PATENT DOCUMENTS

| | | |
|---|---|---|
| CN | 101217859 A1 | 7/2008 |
| JP | 0407169887 A | 7/1995 |

(Continued)

OTHER PUBLICATIONS

Abi-Samra, Kameel et al., "Infrared Controlled Waxes for Liquid Handling and Storage on a CD-Microfluidic Platform", The Royal Society of Chemistry; Lab Chip, 2011, 723-726.

(Continued)

*Primary Examiner* — Bao-Thuy Nguyen
*Assistant Examiner* — Erik B Crawford
(74) *Attorney, Agent, or Firm* — Dorsey & Whitney LLP (57) ABSTRACT

Embodiments of the present invention include methods for conducting agglutination assays using sedimentation. Aggregates may be exposed to sedimentation forces and travel through a density medium to a detection area. Microfluidic devices, such as microfluidic disks, are described for conducting the agglutination assays, as are systems for conducting the assays.

14 Claims, 6 Drawing Sheets

(56) References Cited

U.S. PATENT DOCUMENTS

| | | |
|---|---|---|
| 4,683,579 A | 7/1987 | Wardlaw |
| 4,844,818 A | 7/1989 | Smith |
| 5,000,254 A | 3/1991 | Williams |
| 5,197,858 A | 3/1993 | Cheng |
| 5,279,936 A | 1/1994 | Vorpahl |
| 5,296,775 A | 3/1994 | Cronin et al. |
| 5,297,623 A | 3/1994 | Ogushi et al. |
| 5,335,143 A | 8/1994 | Maling |
| 5,583,746 A | 12/1996 | Wang |
| 5,616,974 A | 4/1997 | Yamada |
| 5,635,362 A | 6/1997 | Levine et al. |
| 5,705,628 A | 1/1998 | Hawkins |
| 5,727,928 A | 3/1998 | Brown |
| 5,736,787 A | 4/1998 | Larimer |
| 5,794,687 A | 8/1998 | Webster et al. |
| 5,882,903 A | 3/1999 | Andrevski et al. |
| 5,957,659 A | 9/1999 | Amou et al. |
| 5,963,887 A | 10/1999 | Giorgio |
| 5,979,541 A | 11/1999 | Saito |
| 6,050,326 A | 4/2000 | Evans et al. |
| 6,078,468 A | 6/2000 | Fiske |
| 6,153,148 A | 11/2000 | Thomas |
| 6,175,495 B1 | 1/2001 | Batchelder |
| 6,194,798 B1 | 2/2001 | Lopatinsky |
| 6,249,071 B1 | 6/2001 | Lopatinsky et al. |
| 6,319,469 B1 | 11/2001 | Mian et al. |
| 6,356,435 B1 | 3/2002 | Davis et al. |
| 6,379,974 B1 | 4/2002 | Parce et al. |
| 6,392,720 B1 | 5/2002 | Kim |
| 6,457,955 B1 | 10/2002 | Cheng |
| 6,503,722 B1 | 1/2003 | Valkirs |
| 6,525,938 B1 | 2/2003 | Chen |
| 6,545,438 B1 | 4/2003 | Mays, II |
| 6,619,385 B2 | 9/2003 | Watanabe et al. |
| 6,623,860 B2 | 9/2003 | Hu et al. |
| 6,638,408 B1 | 10/2003 | Speicher et al. |
| 6,659,169 B1 | 12/2003 | Lopatinsky et al. |
| 6,664,673 B2 | 12/2003 | Lopatnsky et al. |
| 6,685,809 B1 | 2/2004 | Jacobson et al. |
| 6,860,323 B2 | 3/2005 | Cheng |
| 6,873,069 B1 | 3/2005 | Odagiri et al. |
| 6,876,550 B2 | 4/2005 | Sri-Jayantha et al. |
| 6,879,120 B2 | 4/2005 | Xi |
| 6,887,384 B1 | 5/2005 | Frechet et al. |
| 6,955,215 B2 | 10/2005 | Al-Garni et al. |
| 6,960,449 B2 | 11/2005 | Wang et al. |
| 6,966,357 B1 | 11/2005 | Herbert |
| 7,021,894 B2 | 4/2006 | Lopatinsky et al. |
| 7,033,747 B2 | 4/2006 | Gordon |
| 7,035,102 B2 | 4/2006 | Holmes |
| 7,044,202 B2 | 5/2006 | Lopatinsky et al. |
| 7,055,581 B1 | 6/2006 | Roy |
| 7,071,587 B2 | 7/2006 | Lopatinsky et al. |
| 7,100,677 B2 | 9/2006 | Lee et al. |
| 7,134,839 B2 | 11/2006 | Horng et al. |
| 7,136,285 B1 | 11/2006 | Herbert |
| 7,157,049 B2 | 1/2007 | Valencia et al. |
| 7,165,413 B2 | 1/2007 | Symons |
| 7,165,938 B2 | 1/2007 | Lee et al. |
| 7,265,975 B2 | 9/2007 | Tsai |
| 7,267,526 B2 | 9/2007 | Hsu et al. |
| 7,273,091 B2 | 9/2007 | Bahl et al. |
| 7,284,596 B2 | 10/2007 | Larson |
| 7,301,771 B2 | 11/2007 | Hata et al. |
| 7,304,845 B2 | 12/2007 | Xia |
| 7,312,085 B2 | 12/2007 | Chou et al. |
| 7,324,339 B2 | 1/2008 | Foster, Sr. |
| 7,349,212 B2 | 3/2008 | Xia |
| 7,381,027 B2 | 6/2008 | Kaneko et al. |
| 7,455,501 B2 | 11/2008 | Horng et al. |
| 7,458,413 B2 | 12/2008 | Mok |
| 7,481,263 B2 | 1/2009 | Breier et al. |
| 7,520,314 B2 | 4/2009 | Hwang et al. |
| 7,543,457 B2 | 6/2009 | Crocker et al. |
| 7,667,969 B2 | 2/2010 | Khanna et al. |
| 7,670,102 B2 | 3/2010 | Chang et al. |
| 7,695,256 B2 | 4/2010 | Horng et al. |
| 7,758,810 B2 | 7/2010 | Lee et al. |
| 7,836,939 B2 | 11/2010 | Zimmerman et al. |
| 7,896,611 B2 | 3/2011 | Khanna et al. |
| 7,900,690 B2 | 3/2011 | Hawwa et al. |
| 7,905,712 B2 | 3/2011 | Huang |
| 7,911,791 B2 | 3/2011 | Refai-Ahmed et al. |
| 8,322,980 B2 | 12/2012 | Khanna et al. |
| 8,337,775 B2 | 12/2012 | Pugia et al. |
| 2000/0054978 | 2/2000 | Hitachi |
| 2001/0055812 A1 | 12/2001 | Mian et al. |
| 2002/0090307 A1 | 7/2002 | Cheng |
| 2002/0098535 A1 | 7/2002 | Wang et al. |
| 2002/0137068 A1 | 9/2002 | Haugland et al. |
| 2002/0151043 A1 * | 10/2002 | Gordon .................. 435/287.2 |
| 2002/0153251 A1 | 10/2002 | Sassi et al. |
| 2002/0164659 A1 | 11/2002 | Rao et al. |
| 2002/0170825 A1 | 11/2002 | Lee et al. |
| 2003/0013203 A1 | 1/2003 | Jedrzejewski et al. |
| 2003/0124719 A1 | 7/2003 | Woodside |
| 2003/0203504 A1 | 10/2003 | Hefti |
| 2003/0221963 A1 | 12/2003 | Bjellqvist et al. |
| 2004/0035556 A1 | 2/2004 | Jean |
| 2004/0072278 A1 | 4/2004 | Chou et al. |
| 2004/0109291 A1 | 6/2004 | Kannmacher |
| 2004/0114327 A1 | 6/2004 | Sri-Jayantha et al. |
| 2004/0119354 A1 | 6/2004 | Takada |
| 2005/0002163 A1 | 1/2005 | Lopatinsky |
| 2005/0087445 A1 | 4/2005 | Speicher et al. |
| 2005/0117298 A1 | 6/2005 | Koga et al. |
| 2005/0195573 A1 | 9/2005 | Huang |
| 2005/0215410 A1 | 9/2005 | Merino et al. |
| 2005/0274490 A1 | 12/2005 | Larson |
| 2005/0282220 A1 | 12/2005 | Prober et al. |
| 2006/0007656 A1 | 1/2006 | Symons |
| 2006/0021735 A1 | 2/2006 | Lopatinsky |
| 2006/0171654 A1 | 8/2006 | Hawkins et al. |
| 2006/0191792 A1 | 8/2006 | Herr et al. |
| 2007/0000268 A1 | 1/2007 | Crocker et al. |
| 2007/0041158 A1 | 2/2007 | Hornung |
| 2007/0231419 A1 | 10/2007 | Pelcz et al. |
| 2008/0069706 A1 | 3/2008 | Huang |
| 2008/0149484 A1 | 6/2008 | Tolley et al. |
| 2009/0004059 A1 | 1/2009 | Pugia et al. |
| 2009/0069554 A1 | 3/2009 | Finne |
| 2009/0145584 A1 | 6/2009 | Walsh et al. |
| 2009/0166004 A1 | 7/2009 | Cheng-Tien et al. |
| 2009/0209402 A1 | 8/2009 | Andersson |
| 2009/0325186 A1 | 12/2009 | Hinnah et al. |
| 2010/0068754 A1 | 3/2010 | Kirakossian |
| 2010/0120596 A1 | 5/2010 | Froman et al. |
| 2010/0151560 A1 | 6/2010 | Wo et al. |
| 2010/0177480 A1 | 7/2010 | Koplow |
| 2010/0328887 A1 | 12/2010 | Refai-Ahmed et al. |
| 2011/0103011 A1 | 5/2011 | Koplow |

FOREIGN PATENT DOCUMENTS

| | | |
|---|---|---|
| JP | 2000-009090 A1 | 1/2000 |
| JP | 2000-054978 | 2/2000 |
| JP | 2000341902 A1 | 12/2000 |
| JP | 2006-037918 | 2/2006 |
| WO | WO01/68225 A1 | 9/2001 |
| WO | WO04/001845 A1 | 12/2003 |
| WO | WO-2008/143578 | 11/2008 |
| WO | 2009/098237 A1 | 8/2009 |
| WO | WO2009/098237 A1 | 8/2009 |
| WO | WO2010/016963 A1 | 2/2010 |

OTHER PUBLICATIONS

Boyko, Matthew et al., "Cell-Free DNA—A Marker to Predict Ischemic Brain Damage in a Rat Stroke Experimental Model", Neurosurg Anesthesiol; vol. 23, No. 3, Jul. 2011, 222-228.

Carney, J., "Rapid Diagnostic Tests Employing Latex Particles", Analytical Proceedings, Apr. 1990, 99-100.

(56) References Cited

OTHER PUBLICATIONS

Czeiger, David et al., "Measurement of Circulating Cell-Free DNA Levels by a New Simple Fluorescent Test in Patients With Primary Colorectal Cancer", Am J Clin Pathol, 2011, 264-270.
Glorikian, Harry et al., "Smart-Consumables Product Development Strategy: Implications for Molecular Diagnostics", DX Direction, 2010, 12-16.
Goldshtein, Hagit et al., "A Rapid Direct Fluorescent Assay for Cell-Free DNA Quantification in Biological Fluids", Annals of Clinical Biochemistry, 2009, 488-494.
Holmes, David et al., "Leukocyte Analysis and Differentiation Using High Speed Microfluidic Single Cell Impedance Cytometry", Lab Chip 9, Aug. 7, 2009, 2881-2889.
Lee, B. S. et al., "A Fully Automated Immunoassay From Whole Blood on a Disc", Lab Chip 9, Mar. 5, 2009, 1548-1555.
Lim, C. T. et al., "Bead-Based Microfluidic Immunoassays: The Next Generation", Biosens Bioelectron 22, Jul. 20, 2006, 1197-1204.
Lo, Y. M. D. et al., "Plasma DNA as a Prognostic Marker in Trauma Patients", Clinical Chemistry 46:3, 2000, 319-323.
Madou, Marc et al., "Lab on a CD", Annual Rev. Biomed Eng 8, 2006, 601-628.
Maes, Melissa L. et al., "Comparison of Sample Fixation and the Use of LDS-751 or Anti-CD45 for Leukocyte Identification in Mouse Whole Blood for Flow Cytometry", Journal of Immunological Methods, Jan. 30, 2007, 1-13.
Min, Junhong et al., "Functional Integration of DNA Purification and Concentration Into a Real Time Micro-PCR Chip", The Royal Society of Chemistry; Lab Chip, 2011, 259-265.
Price, Christopher P. et al., "Light-Scattering Immunoassay", Principles and Practice of Immunoassay (Second Edition); Chapter 18, 1997, 445-480.
Rhodes, Andrew et al., "Plasma DNA Concentration as a Predictor of Mortality and Sepsis in Critically Ill Patients", Critical Care, 2006, 1-7.
Rider, Todd H. et al., "A B Cell-Based Sensor for Rapid Identification of Pathogens", www.sciencemag.org; Science vol. 301, 2003, 213-215.
Riegger, L. et al., "Read-Out Concepts for Multiplexed Bead-Based Fluorescence Immunoassays on Centrifugal Microfluidic Platforms", Sensors and Actuators a-Physical, 2006, 455-462.
Schaff, Ulrich Y. et al., "Whole Blood Immunoassay Based on Centrifugal Bead Sedimentation", Clinical Chemistry, 2011, 753-761.
Zhang, L. et al., "A New Biodosimetric Method: Branched DNA-Based Quantitative Detection of B1 DNA in Mouse Plasma", The British Journal of Radiology, 83, Aug. 2010, 694-701.
Ziegler, Annemarie et al., "Circulating DNA: A New Diagnostic Gold Mine?", Cancer Treatment Reviews, 2002, 255-271.
Baldwin, Robert L. , "How Hofmeister Ion Interactions Affect Protein Stability", Biophysical Journal; vol. 71, Oct. 1996, pp. 2056-2063.
Curtis, R. A. et al., "A Molecular Approach to Bioseparations: Protein-Protein and Protein-Salt Interactions", Chemical Engineering Science, 2006, pp. 907-923, vol. 61.
Huang and Bergdoll, "The Primary Structure of Staphylococcal Enterotoxin B", The Journal of Biological Chemistry, 25(14), Jul. 1970, pp. 3518-3525.
Agrawal, G., "Foil Air/Gas Bearing Technology—An Overview", American Society of Mechanical Engineers, 1997, Publication 97-GT-347, pp. 1-11.
Ahanotu, et al., "Staphylococcal Enterotoxin B as a Biological Weapon: Recognition, Management, and Surveillance of Staphylococcal Enterotoxin", Applied Biosafety; 11(3), 2006, pp. 120-126.
Air Bearing Application and Design Guide, Rev. D, 2003, New Way Precision—Porous Media Air Bearing Solutions, www.newwayprecision.com, pp. 1-63.
Albrecht, J W. et al., "Micro Free-Flow IEF Enhanced by Active Cooling and Functionalized Gels", Electrophoresis, 2006, pp. 4960-4969, vol. 27.

Amersham, M. "Percoll: Methodology and Applications", 2001, pp. 1-84.
Amukele, et al., "Ricin A-chain activity on stem-loop and unstructured DNA substrates", Biochemistry 44(11), Mar. 25, 2005, pp. 4416-4425.
Berry, Scott M., et al., "One-step Purification of Nucleic Acid for Gene Expression Analysis via Immiscible Filtration Assisted by Surface Tension", Lap Chip, May 21, 2011: 11(10): pp. 1747-1753.
Brigotti, et al., "Shiga toxin 1 acting on DNA in vitro is a heat-stable enzyme not requiring proteolytic activation", Biochimie Journal 86(45), 2004, pp. 305-309.
Cabrera, C R. et al., "Formation of Natural pH Gradients in a Microfluidic Device under Flow Conditions: Model and Experimental Validation", Analytical Chemistry, 2001, pp. 658-666, vol. 73.
Carter, G.I., et al., "Rapid detection of a specific trimethoprim resistance gene using a biotinylated DNA probe", Journal of Antimicrobial Chemotherapy, 20, 1087, pp. 335-341.
Cobb and Saunders, "Heat transfer from a rotating disk", Proceedings of the Royal Society of London, Series A, Mathematical and Physical Sciences, 1956, 236 (1206), pp. 124-130.
Cui, Huanchun et al., "Multistage Isoelectric Focusing in a Polymeric Microfluidic Chip", Analytical Chemistry, Dec. 15, 2005, pp. 7878-7886, vol. 77, No. 24.
Das, C., et al. "Effects of Separation Length and Voltage on Isoelectric Focusing in a Plastic Microfluidic Device", Electrophoresis, 2006, pp. 3619-3626, vol. 27.
Endo, et al., "RNA N-Glycosidase Activity of Ricin A-Chain. Mechanism of Action of the Toxic Lectin Ricin on Eukaryotic Ribosomes", The Journal of Biological Chemistry, 262(17), Jun. 15, 1987, pp. 8128-8130.
Folgea, D. et al., "Detecting Single Stranded DNA with a Solid State Nanopore", Nano Letters, 2005, vol. 5, No. 10, pp. 1905-1909.
Fuller, D., "A Review of the State-of-the-Art for the Design of Self-Acting Gas-Lubricated Bearings", Journal of Lubrication Technology, 1969, 91, pp. 1-16.
Glorikian, H. et al., "Overview of Microfluidic Applications in IVDS", DX Direction 1, 2010, pp. 12-16.
Gorg, A. et al., "Recent Developments in Two-Dimensional Gel Electrophoresis with Immobilized pH Gradients: Wide pH Gradients Up to pH 12, Longer Separation Distances and Simplified Procedures", Electrophoresis, vol. 20, 1999, pp. 712-717.
Gorg, A. et al., "The Current State of Two-Dimensional Electrophoresis with Immobilized pH Gradients", Electrophoresis, vol. 21, 2000, pp. 1037-1053.
Gorkin, et al., "Centrifugal microfluidics for biomedical applications", www.rsc.org/loc, Lab on a Chip, 2010, pp. 1758-1773.
Gusev, I. et al., "Capillary columns with in situ formed porous monolithic packing for micro high-performance liquid chromatography and capillary electrochromatography," J. Chrom. A, 855, 1999, pp. 273-290.
Hatch, A V. et al., "Integrated Preconcentration SDS-PAGE of Proteins in Microchips Using Photopatterned Cross-Linked Polyacrylamide Gels", Analytical Chemistry, vol. 78, 2006, pp. 4976-4984.
Herr, A E. et al., "Microfluidic Immunoassays as Rapid Saliva-Based Clinical Diagnostics", PNAS, vol. 104, No. 13, 2007, pp. 5268-5273.
Herr, A E. et al., "On-Chip Coupling of Isoelectric Focusing and Free Solution Electrophoresis for Multidimensional Separations", Analytical Chemistry, vol. 75, 2003, pp. 1180-1187.
Holmberg and Nygard, "Depurination of A4256 in 28 S rRNA by the Ribosome-inactivating proteins from Barley and Ricin Results in Different Ribosome Conformations," Journal of Molecular Biology: 259(1), May 31, 1996, pp. 81-94.
Huang, T et al., "Microfabrication of a Tapered Channel for Isoelectric Focusing with Thermally Generated pH Gradient", Electrophoresis, vol. 23, 2002, pp. 3504-3510.
International Search Report dated Dec. 24, 2009 for PCT/US2009/044550.
International Search Report dated Mar. 1, 2012 for PCT/US2012/027299.
International Search Report dated Jun. 28, 2013 for PCT/US2013/032349.

(56) References Cited

OTHER PUBLICATIONS

Invitrogen Life Technologies, Instructional Manual, Zoom IEF Fractionator, Cat. Nos. ZF10001 & ZF10002, Version C, Jul. 2004, pp. 1-64.

Lee, B.S., et al. "Fully integrated lab-on-a-disc for simultaneous analysis of biochemistry and immunoassay from whole blood", Lab Chip, 11, 2011 pp. 70-78.

Lim, P., et al., "Rapid isoelectric trapping in a micropreparative-scale multicompartment electrolyzer", Electrophoresis, 2007. vol. 28, pp. 1851-1859.

Lo, C T. et al., "Photoploymerized Diffusion-Defined Ployacrylamide Gradient Gels for On-Chip Protein Sizing", The Royal Society of Chemistry, Lab on a Chip, vol. 8, No. 8, 2008, pp. 1273-1279.

Long, et al., "Integration of nanoporous membranes for sample filtration/preconcentration in microchip electrophoresis", Electrophoresis, 2004, pp. 4927-4934, vol. 27.

O'Farrell, P. H., "High Resolution Two-Dimensional Electrophoresis of Proteins", The Journal of Biological Chemistry, vol. 250, No. 9, 1975, pp. 4007-4021.

Ogle, et al., "Preparative-scale isoelectric trapping separations using a modified Gradiflow Unit", Journal of Chromatorgraphy A, 2002, vol. 979, pp. 155-161.

Riahi, et al., "Molecular Detection of Bacterial Pathogens Using Microparticle Enhanced Double-Stranded DNA Probes", Anal. Chem 83, 2011, pp. 6349-6354.

Righetti, P G. "The Alpher, Bethe, and Gamow of IEF, the Alpha-Centaury of Electrokinetic Methodologies, Part II: Immobilized pH Gradients", Electrophoresis, 2007, pp. 545-555, vol. 28.

Righetti, P G. "The Alpher, Bethe, Gamow of Isoelectric Focusing, the Alpha-Centaury of Electrokinetic Methodologies. Part 1", Electrophoresis, 2006, pp. 923-938, vol. 27.

Salyers, et al., "Use of Randomly Cloned DNA Fragments for Identification of Bacteroides thetaiotaomicron", Journal of Bacteriology, Apr. 1983, 154(1), pp. 187-293.

Satomi, T. et. al., "Design Optimization of Spirally Grooved Thrust Air Gearings for Polygon Mirrow Laser Scanners", The Japan Society of Mechanical Engineers, 1993, Series C., vol. 36(3), pp. 393-399.

Schlichting, H., "Boundary-layer Theory", McGraw-Hill, NY, 1979.

Schembri, et al., "Portable Simultaneous Multiple Analyte Whole-Blood Analyzer for Point-of-Care Testing", Clinical Chemistry 38(9), 1992, pp. 1665-1670.

Sommer, G J. et al., "On-Chip Isoelectric Focusing Using Photopolymerized Immobilized pH Gradients", Analytical Chemistry, 2008, pp. 3327-3333, vol. 80.

Tan, W et al., "Miniaturized Capillary Isoelectric Focusing in Plastic Microfluidic Devices", Electrophoresis, 2002, pp. 3638-3645, vol. 23.

Tennekes, H and Lumley, J., "A First Course in Turbulence", The MIT Press, Cambridge, MA, 1972.

Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer: 19(5), May 15, 1977, pp. 621-626.

Whitney, W., "Theory of the Air-Supported Puck", American Journal of Physicists, 1964, 4, pp. 306-312.

Yu and Hadi, et al., "Bioinformatic processing to identify single nucleotide polymorphism that potentially affect Ape1 function", Mutation Research/Genetic Toxicology and Environmental Mutagenesis: 722(2), Jun. 17, 2011, pp. 140-146.

Zhao and Aoki, "A specific DNA hybridization probe for detection of *Pasteurella piscicida*", Diseases of Aquatic Organisms, vol. 7, 1989, pp. 203-210.

Zilberstein, G. et al., "Parallel Isoelectric Focusing Chip", Proteomics, 2004, pp. 2533-2540, vol. 4.

Zilberstein, G. et al., "Parallel isoelectric focusing II", Electrophoresis 2004, vol. 25, pp. 3643-3651.

Zilberstein, G. et al., "Parallel processing in the isoelectric focusing chip", Electrophoresis, 2003, vol. 24, pp. 3735-3744.

Zuo, X; Speicher, D.W.; "A Method for Global Analysis of Complex Proteomes Using Sample Prefactionation by Solution Isoelectrofocusing Prior to Two-Dimensional Electrophoresis", Analytical Biochemistry, 2000, vol. 284, pp. 266-278.

U.S. Appl. No. 12/891,956 entitled: "Microfluidic Devices, Systems, and Methods for Quantifying Cells Using Centrifugal Force," filed Sep. 28, 2010.

U.S. Appl. No. 12/891,977 entitled, "Devices, Systems, and Methods for Conducting Sandwich Assays Using Sedimentation," filed Sep. 28, 2010.

Andersson, et al., "Parallel nanoliter microfluidic analysis system", Analytical Chemistry, vol. 79, No. 11, 2007, pp. 4022-4030.

Saukkonen, et al., "Cell-Free Plasma DNA as a Predictor of Outcome in Severe Sepsis and Septic Shock", Clinical Chemistry; vol. 54:6, 2008, 1000-1007.

McBain et al., Polyethyleneimine functionalized iron oxide nanoparticles as agents for DNA delivery and transfection, Journal of Materials Chemistry, 17, pp. 2561-2565, available online Apr. 13, 2007.

Molecular Detection of Bacterial Pathogens using Microparticle Enhanced Double-stranded DNA Probes Riahi et al. Analytical Chemistry. 2011. 83(16): 6349-6354 and Supporting Information.

Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.

Quantitative Comparison of Long-wavelength Alexa Fluor Dues to Cy Dyes: Fluorescence of the Dyes and Their Bioconjugates Berlier et al. The Journal of Histochemistry and Cytochemistry. 2003. 51(12): 1699-1712.

\* cited by examiner

SYSTEMS, DEVICES, AND METHODS FOR AGGLUTINATION ASSAYS USING SEDIMENTATION

STATEMENT REGARDING RESEARCH & DEVELOPMENT

Described examples were made with Government support under Government Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

TECHNICAL FIELD

Embodiments of the invention relate generally to agglutination assays utilizing sedimentation forces, and include embodiments utilizing disk-based microfluidics.

BACKGROUND

Agglutination assays may be used to detect the presence of or measure an amount of an analyte in a sample. Typical applications include testing blood serum for the presence of reactive antibodies to known pathogens or testing blood antigen type for donor compatibility. Analytes present in the sample cause particles (e.g. beads) in the sample to interact with each other to form clumps (also called agglutinate or aggregates). Agglutination assays are typically conducted by adding a sample of interest to a suspension of antibody- or antigen-coated particles deposited on a card, and rocking the card manually for a few minutes to facilitate agglutination (clumping). Specific interaction between the antibody/antigen with substances of interest in the sample causes visible aggregation of the particles which serves as the assay readout.

Therefore, a typical agglutination assay is only able to report whether analyte concentration in a sample is above or below a given threshold value (e.g. there are visible clumps of agglutinate or there are not). Furthermore, manual mixing of assay particles and sample by rocking a card can result in a considerable variability of assay conditions yielding a large uncertainty range in the threshold value. Therefore, agglutination assays are typically performed only for applications where the analyte is either present in large quantities in the sample or otherwise almost entirely absent.

DETAILED DESCRIPTION

Certain details are set forth below to provide a sufficient understanding of embodiments of the invention. However, it will be clear to one skilled in the art that embodiments of the invention may be practiced without various of these particular details or with additional details. In some instances, well-known microfluidic device components, processing techniques, detection sensors and systems components, circuits, control signals, timing protocols, and software operations have not been shown in detail in order to avoid unnecessarily obscuring the described embodiments of the invention.

As described above, agglutination assays are typically only used where the analyte is either present in large quantities in a sample or otherwise almost entirely absent, due to the challenges in conducting a reliable, sensitive agglutination assay. For applications requiring higher sensitivity and more precise knowledge of analyte concentration, it may be necessary to detect and quantify microscopic aggregates within the assay particle suspension (e.g. not reliably visible aggregates). Several methods for quantifying agglutination assays have been developed including measuring changes in light scattering caused by formation of microaggregates. However, these methods tend to increase required sample and reagent volumes or introduce complex instrumentation rendering them less useful for low cost assays.

Embodiments of the present invention include agglutination assays utilizing sedimentation. As will be described further below, example agglutination assays may provide improved detection and/or quantification of analyte present in a sample. The improved detection and/or quantification may be due in part to the manner in which the assay is conducted, and/or the device or system used to conduct the agglutination assay. Although improvement is described relative to typical assays, the advantages or improvements achieved by examples of the present invention are provided herein to aid in the understanding of the disclosure, and it is to be understood that not all embodiments of the present invention may provide all, or any, of the improvements or advantages described herein.

Agglutination assays utilizing sedimentation described herein may be used to detect and/or quantify an analyte in a sample. Any of a variety of suitable samples may be used including, but not limited to, whole blood, buffer solutions, or other biological fluid samples. The biological fluid may be combined with buffer or other fluids to form the sample. Generally, the sample may include analytes of interest to be detected and/or quantified in accordance with embodiments of the present invention.

Analytes of interest may include chemicals and/or molecules that are of interest for detection in a sample. Any of a variety of analytes of interest may be detected in accordance with embodiments of the present invention, including proteins, RNA, and/or DNA.

Agglutination assays in accordance with embodiments of the present invention may occur in part using sedimentation. Sedimentation generally refers to the process of movement of a particle or substance under an influence of a gravitational field. Sedimentation forces may be generated due to gravity or centrifugal forces, for example.

Examples of agglutination assays described herein may be used to detect the presence of an analyte of interest. Accordingly, a detection signal received from appropriate detection area may indicate the presence of the analyte of interest in the sample, as will be described further below. In some examples, the detection signal may be required to be above a threshold value to indicate presence of the analyte of interest in the sample to avoid possible positives should some detection signal be received from the detection area due to other factors unrelated to the assay.

Examples of agglutination assays described herein may be used to quantify an amount of analyte of interest present in a sample. A magnitude or strength of a detection signal from an appropriate detection area may be indicative of the amount of analyte present in the sample.

Examples of agglutination assays utilizing sedimentation described herein may utilize coated particles. Any particles suitable for conducting agglutination assays may be used, including but not limited to, beads such as polystyrene beads or silica beads. Substantially any bead radii may be used. Examples of beads may include beads having a radius ranging from 150 nanometers to 10 microns. Other sizes may also be used.

The particles (e.g. beads) may be coated with affinity reagents. The affinity reagent may be any suitable reagent for binding to an analyte of interest. Suitable reagents include antibodies for binding to one or more proteins, antigens, and DNA probes for binding to DNA and/or mRNA in a fluid sample. To facilitate agglutination assays, the affinity reagents may be able to recognize multiple sites on the analyte of interest. In this manner, multiple particles may bind to a single analyte of interest at different locations, facilitating aggregate formation. Examples of affinity reagents able to recognize multiple sites on the analyte of interest include polyclonal antibodies, antigens with multiple potential binding sites, mixtures of monoclonal antibodies with different recognition sites, and mixtures of nucleotide probes with different hybridization sites. The affinity reagents may be coated on the particles in generally any suitable matter. In some examples, beads may be commercially available coated with appropriate affinity reagents.

Some of the particles may be labeled with a label (e.g. a tag) suitable for detection. Fluorescent tags (e.g. fluorophores) may provide an optical detection signal, however colorimetric or radioactive tags may also be used. In some examples, the particle itself may serve as the label, e.g. fluorescent beads.

Examples of agglutination assays utilizing sedimentation described herein may utilize density media. Density medium (also referred to as density media herein) is generally a liquid which may have a density selected based on the sample or coated particles, as described further herein. The density media may generally be implemented using a fluid having the selected density. In some examples, a fluid sample may be diluted for use with a particular density media. The density media may include, for example, a salt solution containing a suspension of silica particles which may be coated with a biocompatible coating. An example of a suitable density media is Percoll™, available from GE Lifesciences. Particular densities may be achieved by adjusting a percentage of Percoll™ in a salt solution. More generally, viscosity and density may be adjusted by changing a composition of the media. Varying the concentration of solutes such as, but not limited to, sucrose or dextran, in the density media, may adjust the density and/or viscosity of the media. In some embodiments, the density media may include a detergent, such as Tween 20. The detergent may enhance a wash function of transport through the density media.

Figure 1:
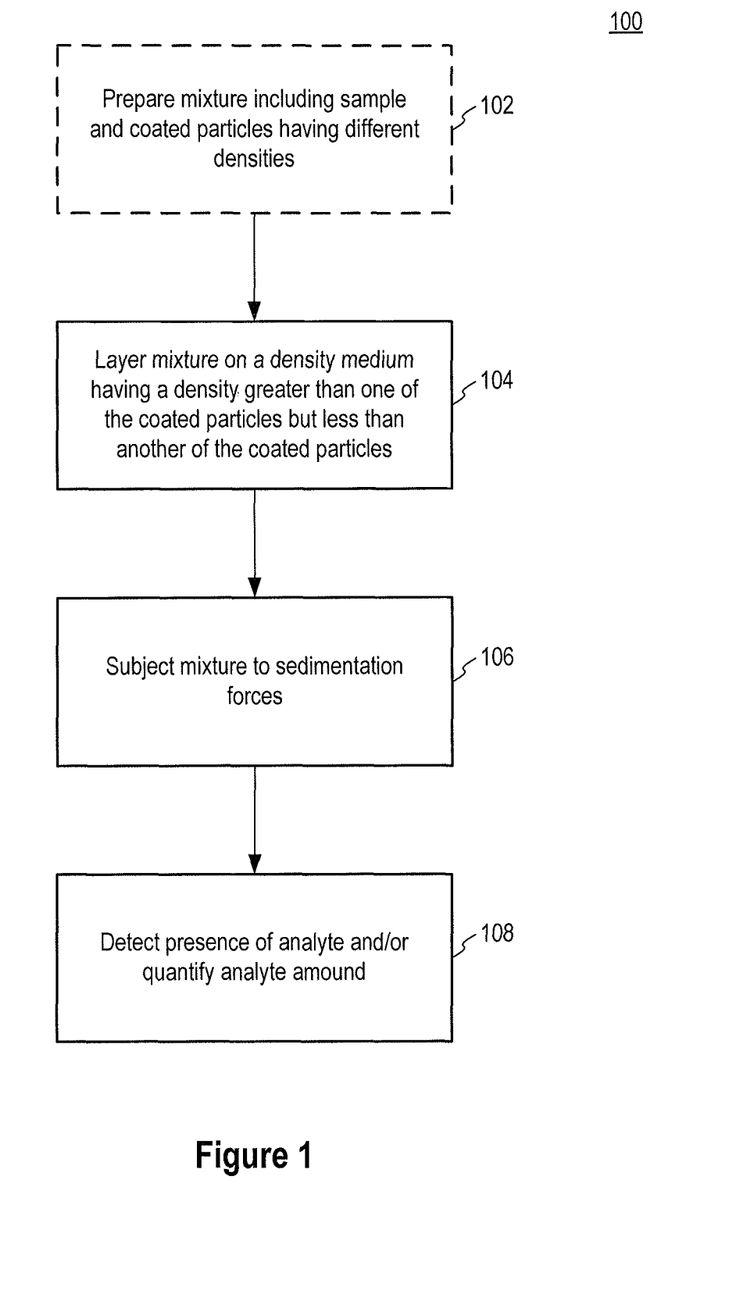
FIG. 1 is a flowchart of an example of a method for conducting an agglutination assay in accordance with embodiments of the present invention.

FIG. 1 is a flowchart of an example of a method for conducting an agglutination assay in accordance with embodiments of the present invention. In block 102, a mixture may be prepared including the sample and coated particles having different densities. Block 102 may be optional in some examples. In block 104, the mixture may be layered on a density medium having a density greater than one of the coated particles and smaller than another of the coated particles. Agglutination may occur, if suitable analytes are present in the sample, to form aggregates of analyte in the sample and particles in the mixture. In block 106, the mixture may be subject to sedimentation forces. If aggregates are present, they may sediment through the density medium to a detection area. If aggregates are not present, the particles having a density less than the density medium may remain layered on the density medium and may not sediment through the density medium. In some examples, the particles having a density less than the density medium may be labeled for detection. Accordingly, if the particles having a density less than the density medium are not sedimented through to the detection area, no analyte may later be detected. In block 108, the presence of the analyte may be detected in the detection area and/or quantified. In this manner, aggregates too small to be detected visually may also be collected at the detection are and contribute to the detection and/or quantification of the analyte of interest. It is to be understood that additional blocks may be present in some examples. Moreover, aggregates may be formed at any time during the method.

Figure 2:
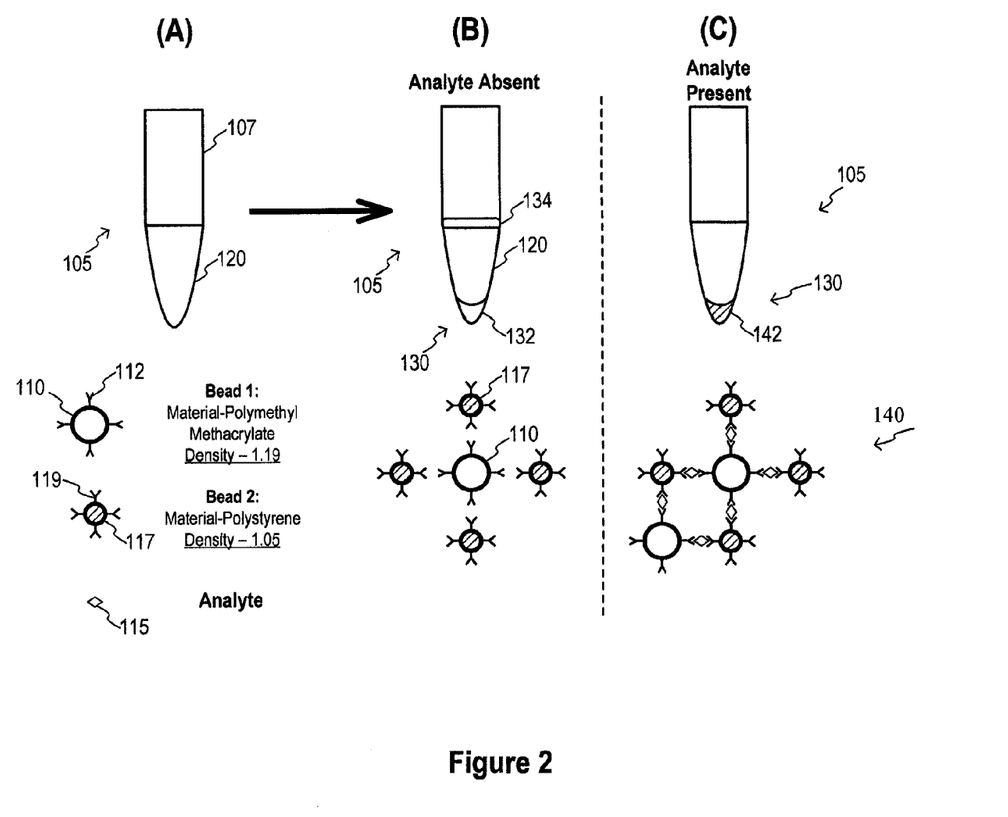
FIGS. 2A-2C are schematic illustrations of different stages of agglutination assays in accordance with embodiments of the present invention.

Example methods arranged in accordance with the flowchart shown in FIG. 1 are further described with reference to FIGS. 2A-2C. FIGS. 2A-2C are schematic illustrations of different stages of agglutination assays in accordance with embodiments of the present invention. The embodiments of the present invention represented in FIGS. 2A-2C may occur during performance of a method according to FIG. 1, e.g. utilize a density-based mechanism for conducting an agglutination assay.

Recall in block 102 of FIG. 1, a mixture may be prepared including a sample and coated particles having different densities. The sample may or may not include the analyte of interest. Generally, one population of particles may be included in the mixture that may have a density greater than the density medium used in the assay, and another population of particles may be included in the mixture that may have a density less than the a density of the density medium used in the assay. The mixture may be prepared by mixing the particles with the sample, by introducing the sample into a mixture already containing one or both population of particles, or through other combinations. In some examples, the mixture is already provided.

FIG. 2A illustrates the mixture 107 contained in a device 105. The device 105 may, for example, be implemented as a vial or a microfluidic device, as will be described further below. The mixture 107 includes a sample and coated particles (e.g. beads) having different densities. The example of FIG. 2A illustrates two bead populations. A first bead population may include the bead 110, shown schematically in FIG. 2A below the schematic depiction of the device 105. The bead 110 may have a density greater than the density media. In the example of FIG. 2A, the bead 110 may be implemented as a polymethyl methacrylate bead having a density of approximately 1.19 g/cm$^3$ and diameter of 1 µm. The bead 110 may be coated with affinity reagents, including the affinity reagent 112, which may be selected to bind with a particular analyte of interest. An analyte of interest 115 is also shown schematically in FIG. 2A.

A second bead population may include the bead 117. The bead 117 may have a density less than a density of the density media. In the example of FIG. 2A, the bead 117 may be implemented as a fluorescent polystyrene bead having a density of approximately 1.05 g/cm$^3$ and diameter of 1 μm. The bead 117 may be coated with affinity reagents, including the affinity reagent 119, which may be selected to bind with the particular analyte of interest in such a way as to form an agglutinate with the bead 110 and the analyte 115. The second population of beads having a density less than that of the density media, including the bead 117, may also be labeled with a detection label. As described above, the detection label may include a fluorescent label, chemical label, electronic label, or combinations thereof. As will be described further, detection of the detection label in a detection area may be indicative of the presence of the analyte of interest. Accordingly, embodiments of the invention include providing a mixture of low density labeled beads and high density unlabeled beads.

Accordingly, FIG. 2A illustrates a mixture 107 which may include a sample, and coated particles including bead 110 and bead 117. The sample may include the analyte of interest 115 or may not. The amount of bead populations provided in the mixture may vary. Generally, sufficient amounts of each bead population are provided to generate aggregates for the expected amount of analyte in the sample.

Referring back to FIG. 1, in block 104, the mixture may be layered on a density medium having a density greater than one of the coated particles but less than another of the coated particles. As described with reference to FIG. 2A, the mixture may include a first population of particles having approximately one density greater than a density of the density media and a second population of particles having approximately another density less than the density of the density media. The mixture may be layered on the density medium by providing the mixture in fluid communication with the density medium such that aggregates may pass through the density medium responsive to sedimentation forces. For example, the mixture may be loaded into a device such that the mixture is next to the density medium, on top of the density medium, or separated from the density medium by other fluids or device components.

Referring to FIG. 2A, the mixture 107 is loaded into the device 105 such that it is adjacent the density media 120. For example, if the device 105 is implemented as a vial, the mixture 107 may be pipetted or otherwise dispensed on top of the density media 120. If the device 105 is implemented as a microfluidic device, the mixture 107 may be introduced to the device next to the density media 120. In other examples, fluids or device features may separate the density media 120 and the mixture 107, however, the aggregates may travel across those intervening fluids or features to allow sedimentation of aggregates.

Following block 104 of FIG. 1, in some examples, an incubation period may be provided to allow aggregates to form. In other examples, aggregates may have already formed in the mixture during introduction to a device or prior to introduction to the device. In other examples, aggregates form or continue to form following further blocks of the method. As described above, aggregates may form when the analyte of interest is present in the sample and may not form if the analyte of interest is not present.

Referring back to FIG. 1, in block 106, the mixture may be subjected to sedimentation forces. In some examples, the mixture may be subjected to sedimentation forces using gravity. In other examples, the mixture may be subjected to sedimentation forces using centrifugal forces. Referring to FIG. 2A, in examples where the device 105 is a vial, the vial may be left to incubate in a gravitational field, allowing sedimentation of aggregates, if present, in the mixture 107. Alternatively, the vial may be placed in a centrifuge and the centrifuge spun to allow sedimentation of the aggregates, if present, in the mixture 107.

FIG. 2B is a schematic illustration of the device 105 following exposure to sedimentation forces when no aggregate has formed in the mixture, which may be an indication that no analyte of interest is present in the sample. The lack of aggregate formation is indicated schematically below the device 105 in FIG. 2B. The bead populations, including bead 110 and 117, have not formed aggregates by binding with target analyte, since no analyte or insufficient analyte, is present in the sample. Accordingly, these bead populations remain unbound in the mixture. Following exposure to sedimentation forces, the particles (e.g. beads) having a density greater than the density medium may sediment through the density medium to a detection area 130. Accordingly, the bead population 132, including the bead 110 for example, may be found in the detection area 130 following sedimentation. However the particle (e.g. bead) population that is less dense than the density medium may not travel through the density medium responsive to the sedimentation forces, and following sedimentation the bead population 134, including the bead 117 for example, may not be found at the detection area and may instead be located, for example, above or adjacent to the density medium 120, as shown in FIG. 2B. Recall that the bead population 134, which includes beads that are less dense than the density medium, may include the detection label. Accordingly, the detection label in the example of FIG. 2B may not be found at the detection area 130, and may not contribute to a detection signal measured at the detection area 130.

FIG. 2C is a schematic illustration of the device 105 following exposure to sedimentation forces when aggregate has formed in the mixture, which may be an indication that analyte of interest is present in the sample. The aggregate formation is indicated schematically below the device 105 in FIG. 2C. The bead populations, including bead 110 and 117, may form aggregates, including the aggregate 140. The aggregates are formed in part because the analytes of interest bind to both the bead populations. The analytes of interest, as generally described above, may bind to the bead populations of interest at respective different sites of the analyte. Accordingly, the analyte 115 of FIG. 2C is shown bound to the beads 110 and 117. The aggregates, including the aggregate 140, will be denser than the density media and will accordingly travel through the density media responsive to the sedimentation forces. Accordingly, following sedimentation, aggregates, including the aggregate 140 may be present in a pellet 142 in the detection area 130. The aggregates include the beads having a detection label, such as the bead 117, and accordingly, the pellet 142 may be detected by detecting the detection label. Aggregates too small to be visually identified individually may still sediment into the pellet and accumulate into a detectable mass, which may result in improved detection capability relative to techniques relying on visual identification of aggregates. An amount of the detection label detected may correspond with an amount of the analyte of interest present in the sample. Because aggregates have formed, no beads or fewer beads are present at the interface between the mixture and the density medium. There may be some labeled beads present at the interface, however, if not all of the labeled beads formed aggregates, such as may be the case if there is a smaller amount of analyte present in the sample.

Referring back to FIG. 1, recall in block 108 the presence of the analyte of interest may be detected and/or quantified. The detection process will vary based, in part, on the detection label used. For example, if a fluorescence label is used, an optical detector may be used to detect the presence of the analyte by detecting the pellet 142 in the detection area 130 of FIG. 2C. If an electronic label is used, an electrical detector, including suitable electrode(s), current and/or voltage supplies and circuitry, may be positioned to detect the electrical detection label in the detection area 130. Other detection modes may also be used. In some examples, the presence of a detection signal generated by a detector may be used to determine the analyte of interest is present in the sample. In some examples, a magnitude or strength of the detection signal may be used to quantify an amount of analyte present in the sample. In some examples, the detection signal from agglutinates may be integrated to quantify the amount of analyte of interest in the sample. In some examples, a volume of the pellet may be measured to quantify the amount of analyte of interest in the sample.

Figure 3:
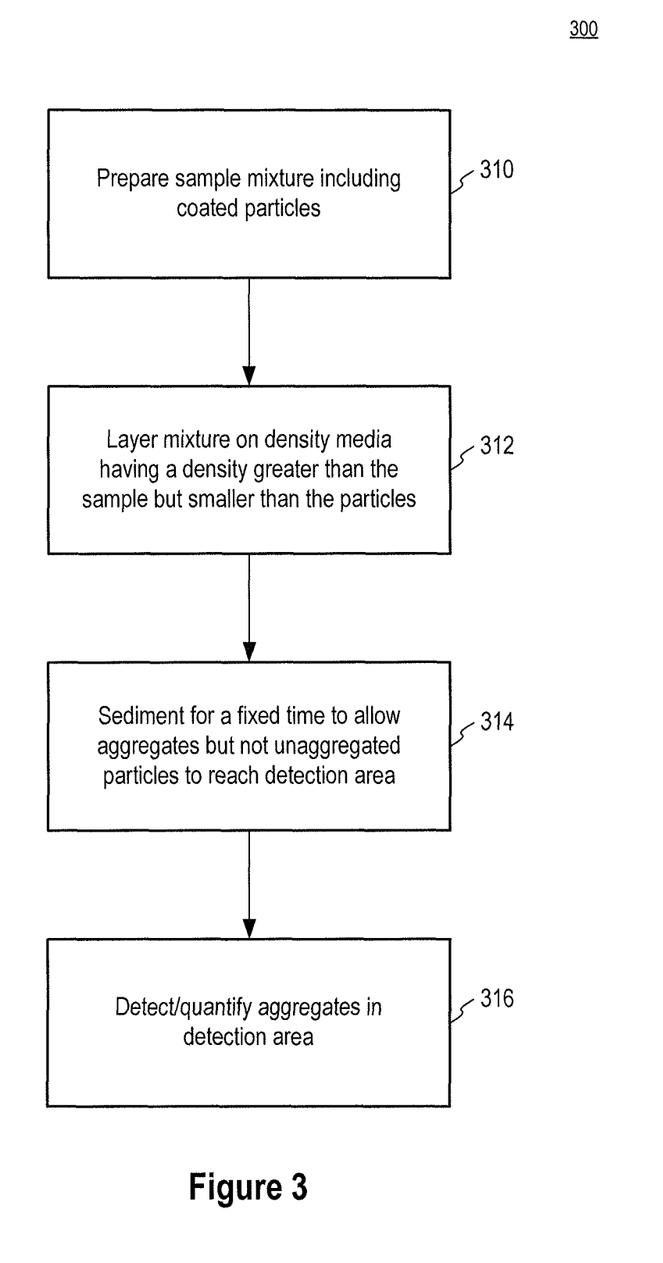
FIG. 3 is a flowchart of another example of a method for conducting an agglutination assay in accordance with embodiments of the present invention.

FIG. 3 is a flowchart of another example of a method for conducting an agglutination assay in accordance with embodiments of the present invention. The method 300 may include in block 310, preparing a mixture including coated particles. The density of coated particles in embodiments in accordance with FIG. 3 may be greater than a density medium used in examples of the invention. In block 312, the mixture may be layered on a density medium having a density greater than the sample but smaller than the particles. Aggregates of analyte and particles may form if analytes of interest are present in the sample. In block 314, the mixture may be subjected to sedimentation forces for a fixed time to allow aggregates, but not unaggregated particles, to reach a detection area. For example, the aggregates are larger than the unbound particles. Accordingly, when subjected to sedimentation forces, the aggregates may travel through the density medium faster than unbound particles. Accordingly, there is a sedimentation time where aggregates will be expected to have arrived at a detection location, but unbound particles would not be expected to arrive at the detection location. Generally, particle sedimentation rate increases with the square of particle size, and this relationship may be used to determine the sedimentation time. In block 316, aggregates may be detected in the detection area. The aggregates may be detected using a label on the particles, such as but not limited to, a fluorescent, electrical, or chemical label as has been described above. In this manner, aggregates too small to be detected visually may also be collected at the detection area and contribute to the detection and/or quantification of the analyte of interest. It is to be understood that additional blocks may be present in some examples. Moreover, aggregates may be formed at any time during the method.

Figure 4:
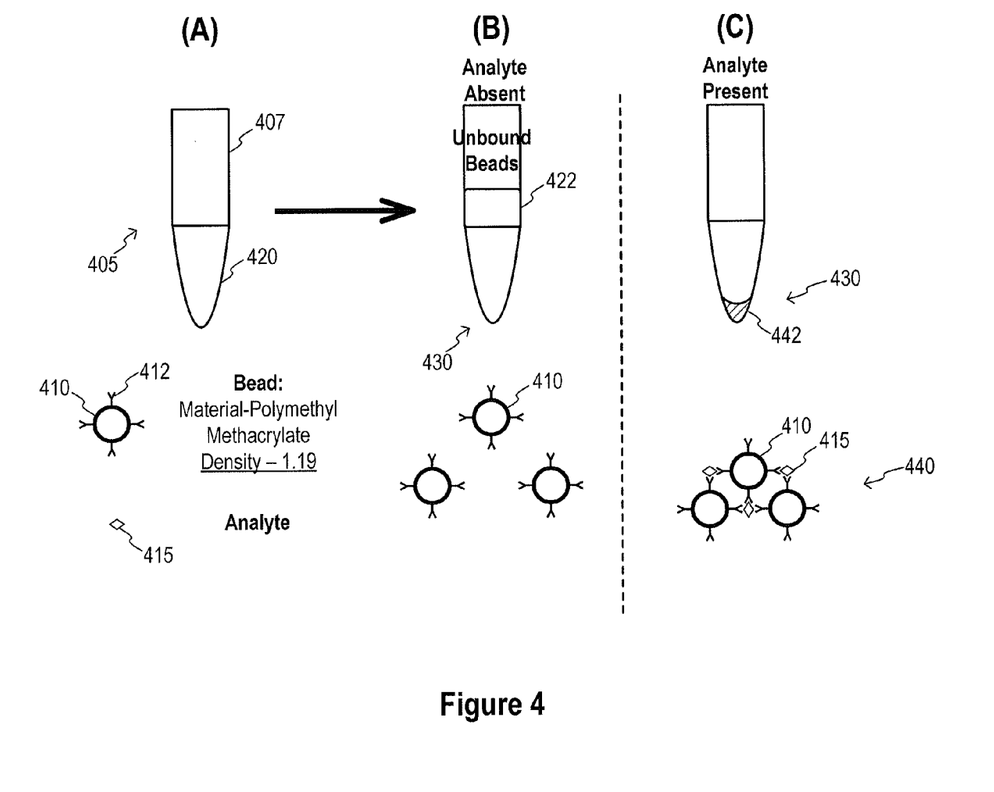
FIGS. 4A-4C are schematic illustrations of different stages of agglutination assays in accordance with embodiments of the present invention.

Example methods arranged in accordance with the flowchart shown in FIG. 3 are further described with reference to FIGS. 4A-4C. FIGS. 4A-4C are schematic illustrations of different stages of agglutination assays in accordance with embodiments of the present invention. The embodiments of the present invention represented in FIGS. 4A-4C may occur during performance of a method according to FIG. 3, e.g. utilize a size-based mechanism for conducting an agglutination assay.

Recall in block 310 of FIG. 3, a mixture may be prepared including a sample and coated particles. The sample may or may not include the analyte of interest. Generally, the particles included in the mixture may have a density greater than the density medium used in the assay. The mixture may be prepared by mixing the particles with the sample, by introducing the sample into a mixture already containing the particles, or through other combinations. In some examples, the mixture is already provided and the block 310 is optional.

FIG. 4A illustrates the mixture 407 contained in a device 405. The device 405 may, for example, be implemented as a vial or a microfluidic device, as will be described further below. The mixture 407 includes a sample and coated particles (e.g. beads). The particles are coated with affinity reagents for the analyte of interest, as has been described above. The example of FIG. 4A illustrates the bead 410 schematically shown below the schematic depiction of the device 405. The bead 410 may have a density greater than the density media. In the example of FIG. 4A, the bead 410 may be implemented as a polystyrene bead having a density of approximately 1.05 g/cm$^2$ and diameter of 1 μm. The bead 410 may be coated with affinity reagents, including the affinity reagent 412, which may be selected to bind with a particular analyte of interest. An analyte of interest 415 is also shown schematically in FIG. 4A. The particles (e.g. beads) may also be labeled with a detection label. As described above, the detection label may include a fluorescent label, chemical label, electronic label, or combinations thereof. As will be described further, detection of the detection label in a detection area may be indicative of the presence of the analyte of interest.

Accordingly, FIG. 4A illustrates a mixture 407 which may include a sample and coated particles including bead 410. The sample may include the analyte of interest 415 or may not. The amount of beads provided in the mixture may vary. Generally, sufficient amounts of beads are provided to generate aggregates for the expected amount of analyte in the sample.

Referring back to FIG. 3, in block 312, the mixture may be layered on a density medium having a density greater than the sample but less than the coated particles. As described with reference to FIG. 4A, the mixture may include particles having a density greater than a density of the density medium. The mixture may be layered on the density medium by providing the mixture in fluid communication with the density medium such that aggregates may pass through the density medium responsive to sedimentation forces. For example, the mixture may be loaded into a device such that the mixture is next to the density medium, on top of the density medium, or separated from the density medium by other fluids or device components.

Referring to FIG. 4A, the mixture 407 is loaded into the device 405 such that it is adjacent the density media 420. For example, if the device 405 is implemented as a vial, the mixture 407 may be pipetted or otherwise dispensed on top of the density medium 420. If the device 405 is implemented as a microfluidic device, the mixture 407 may be introduced to the device next to the density medium 420. In other examples, fluids or device features may separate the density medium 420 and the mixture 407, however, the aggregates may travel across those intervening fluids or features to allow sedimentation of aggregates.

Following block 312 of FIG. 3, in some examples, an incubation period may be provided to allow aggregates to form. In other examples, aggregates may have already formed in the mixture during introduction to a device or prior to introduction to the device. In other examples, aggregates form or continue to form following further blocks of the method. As described above, aggregates may form when the analyte of interest is present in the sample and may not form if the analyte of interest is not present.

Referring back to FIG. 3, in block 314, the mixture may be subjected to sedimentation forces for a fixed time. In some examples, the mixture may be subjected to sedimentation forces using gravity. In other examples, the mixture may be subjected to sedimentation forces using centrifugal forces.

The time is selected based on the relative speed of travel of the unbound particles and aggregates through the density medium. The speed of travel will be related to the size of the unbound particles and aggregates, respectively, as well as the density of the density medium and particles. The time selected may also be based on the distance between the sample and the detection area. Generally, the time is selected to allow the aggregates to reach the detection area, but not the unbound particles. Referring to FIG. 4A, in examples where the device 405 is a vial, the vial may be left to incubate in a gravitational field, allowing sedimentation of aggregates, if present, in the mixture 407. Alternatively, the vial may be placed in a centrifuge and the centrifuge spun to allow sedimentation of the aggregates, if present, in the mixture 407.

FIG. 4B is a schematic illustration of the device 405 following exposure to sedimentation forces when no aggregate has formed in the mixture, which may be an indication that no analyte of interest is present in the sample. The lack of aggregate formation is indicated schematically below the device 405 in FIG. 4B. The beads, including bead 410, have not formed aggregates by binding with target analyte, since no analyte or insufficient analyte, is present in the sample. Accordingly, these beads remain unbound in the mixture and travel slowly relative to the speed aggregates would travel through the density medium. Following exposure to sedimentation forces, the particles (e.g. beads) may sediment through the density medium but not reach a detection area because insufficient time was provided for the unbound beads to reach the detection area 430. Accordingly, the beads may be found in an area 422 following sedimentation that may be partially between the initial location of the sample and the detection area 430. However the particles (e.g. beads) may not be found at the detection area. Recall that the beads may include a detection label. Accordingly, the detection label in the example of FIG. 4B may not be found at the detection area 430, and may not contribute to a detection signal measured at the detection area 430.

FIG. 4C is a schematic illustration of the device 405 following exposure to sedimentation forces when aggregate has formed in the mixture, which may be an indication that analyte of interest is present in the sample. The aggregate formation is indicated schematically below the device 405 in FIG. 4C. The beads, including bead 410, may form aggregates, including the aggregate 440. The aggregates are formed in part because the analytes of interest bind to both the bead populations. The analytes of interest, as generally described above, may bind to the beads at respective different sites of the analyte. Accordingly, the analyte 415 of FIG. 4C is shown bound to multiple beads, including the bead 410. The aggregates, including the aggregate 440, are larger than the unbound beads and will accordingly travel faster through the density media 420. Accordingly, following sedimentation, aggregates, including the aggregate 440 may be present in a pellet 442 in the detection area 430. The aggregates include the beads having a detection label, such as the bead 410, and accordingly, the pellet 442 may be detected by detecting the detection label. Aggregates too small to be visually identified individually may still sediment into the pellet and accumulate into a detectable mass, which may result in improved detection capability relative to techniques relying on visual identification of aggregates. An amount of the detection label detected may correspond with an amount of the analyte of interest present in the sample. Any unbound beads will not have reached the detection area 430 due to the fixed time selected for sedimentation, and accordingly unbound beads may not contribute to the detection signal.

Referring back to FIG. 3, recall in block 316 the presence of the analyte of interest may be detected and/or quantified. The detection process will vary based, in part, on the detection label used. For example, if a fluorescence label is used an optical detector may be used to detect the presence of the analyte by detecting the pellet 442 in the detection area 430 of FIG. 4C. The lack of analyte may also be detected by detecting a sufficient amount of label in an area other than the detection area 430, such as by detecting the unbound beads that have not yet reached the detection area 430. If an electronic label is used, an electrical detector, including suitable electrode(s), current and/or voltage supplies and circuitry, may be positioned to detect the electrical detection label in the detection area 430. Other detection modes may also be used. In some examples, the presence of a detection signal generated by a detector may be used to determine the analyte of interest is present in the sample. In some examples, a magnitude or strength of the detection signal may be used to quantify an amount of analyte present in the sample. In some examples, the detection signal from agglutinates may be integrated to quantify the amount of analyte of interest in the sample. In some examples, a volume of the pellet may be measured to quantify the amount of analyte of interest in the sample.

Figure 5:
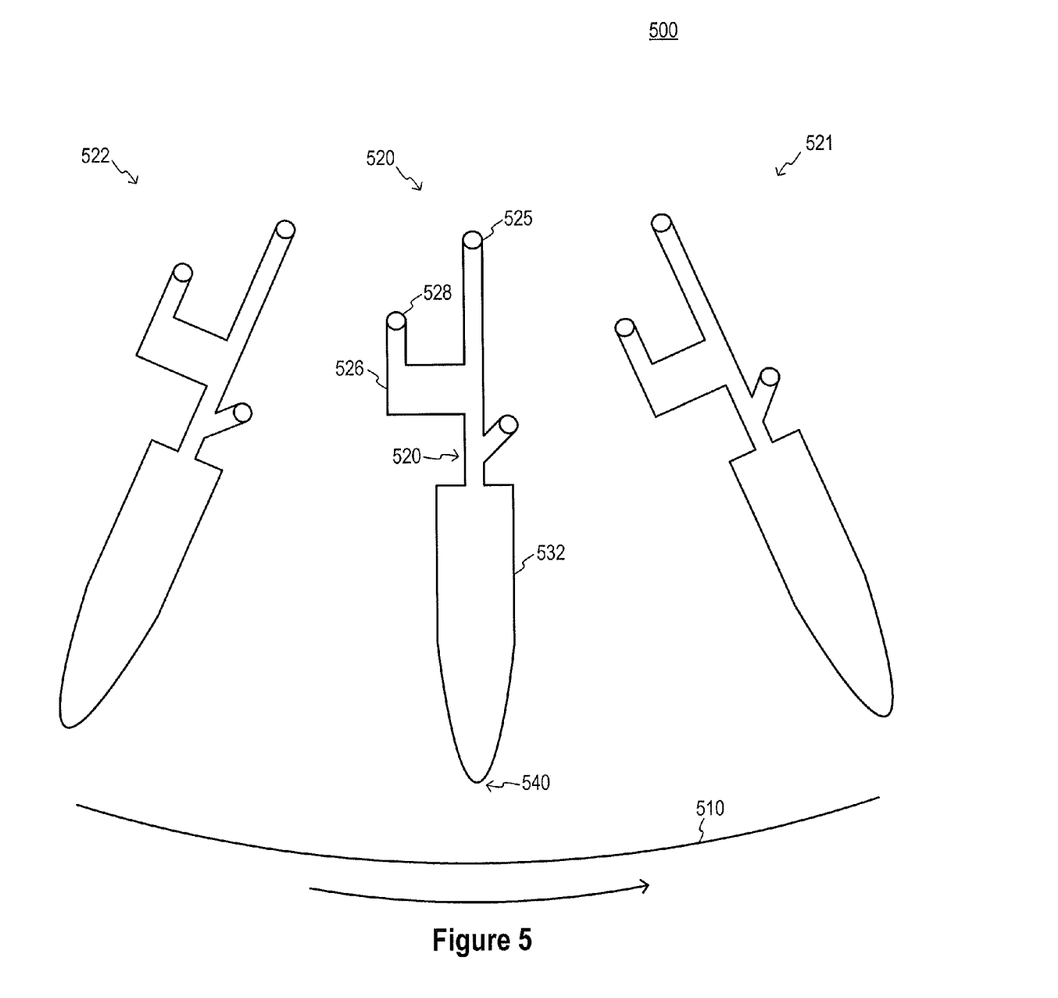
FIG. 5 is a schematic illustration of a microfluidic device arranged in accordance with an embodiment of the present invention.

FIG. 5 is a schematic illustration of a microfluidic device arranged in accordance with an embodiment of the present invention. The device 500 is implemented as a microfluidic disk, however in other examples of the present invention, a disk may not be used and the device 500 may have another form factor. The microfluidic device 500 may include a substrate 510 which may at least partially define regions of assay areas 520, 521, and 522.

The substrate 510 may be implemented using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the device 500. In some embodiments, however, opaque plastic, metal or semiconductor substrates may be used. In some embodiments, multiple materials may be used to implement the substrate 510. The substrate 510 may include surface treatments or other coatings, which may in some embodiments enhance compatibility with fluids placed on or within the substrate 510. In some embodiments surface treatments or other coatings may be provided to control fluid interaction with the substrate 510. While shown as a round disk in FIG. 5, the substrate 510 may take substantially any shape, including square.

In some embodiments, as will be described further below, the substrate 510 may itself be coupled to a motor for rotation. In some embodiments, the substrate may be mounted on another substrate or base for rotation. For example, a microfluidic chip fabricated at least partially in a substrate may be mounted on another substrate for spinning. In some examples, the microfluidic chip may be disposable while the substrate or base it is mounted on may be reusable. In some examples, the entire disc may be disposable. In some examples, a disposable cartridge including one or more microfluidic channels may be inserted into disk or other mechanical rotor that forms part of a detection system.

The substrate 510 may generally, at least partially, define a variety of fluidic features. The fluidic features may be microfluidic features. Generally, microfluidic, as used herein, refers to a system, device, or feature having or including a feature having a dimension of around 1 mm or less and suitable for at least partially containing a fluid. In some embodiments, the microfluidic features may have a dimension of around 100 μm or less. Other dimensions may be used. The substrate 510 may define one or more fluidic features, including any number of channels, chambers, inlet/outlet ports, or other features.

Microscale fabrication techniques, generally known in the art, may be utilized to fabricate the microfluidic device 500. The microscale fabrication techniques employed to fabricate the device 500 may include, for example, embossing, etching, injection molding, surface treatments, photolithography, bonding and other techniques.

Multiple assay areas including assay areas 520, 521, and 522 may be supported by the substrate 510. The multiple assay areas allow multiple assays to be conducted in parallel. For example, a different sample may be introduced to each of the assay areas 520, 521, and 522, and three assays conducted on the assay areas may each include the fluidic features and components for performing an agglutination assay in accordance with examples of the present invention. The features of the assay area 520 are now further described. A fluid inlet port 525 may be provided to receive a fluid that may be analyzed using the microfluidic device 500. The fluid inlet port 525 may have generally any configuration, and a fluid sample may enter the fluid inlet port 525 utilizing substantially any fluid transport mechanism, including pipetting, pumping, or capillary action. The fluid inlet port 525 may take substantially any shape. Generally, the fluid inlet port 525 is in fluid communication with a mixing chamber 526. Generally, by fluid communication it is meant that a fluid may flow from one area to the other, either freely or using one or more transport forces and/or valves, and with or without flowing through intervening structures.

The mixing chamber 526 may be a feature configured to allow for the sample and particles to mix with each other and/or with additional fluids (e.g. buffers, reagents, etc.). Another fluid inlet port 528 may be in fluid communication with the mixing chamber 526 for the introduction of coated particles or other species into the mixing chamber 526. Accordingly, during operation, sample fluid may be introduced to the mixing chamber 526 through the fluid inlet port 525 and coated particles, which may be suspended in a buffer or other fluid, may be introduced to the mixing chamber 526 through the inlet port 528, or may already be present in the mixing chamber 526. It is to be understood that the form factor and layout of the microfluidic components described herein is quite flexible, and for example, the mixing chamber 526 may take substantially any form factor including a chamber, reservoir, or channel. The mixing chamber 526 generally refers to a portion of the microfluidic device 500 suitable for holding sample fluid and coated particles. A mixer may be included in some embodiments to mix fluids contained in the mixing chamber 526.

A valve 530 is provided for fluidic separation between the mixing chamber 526 and reservoir 532. The valve 530 may be used to contain fluids in the mixing chamber 526 for a period of time to allow the fluids to mix (e.g. sample and coated particles), and may then be opened to allow the mixture into the reservoir 532. Any suitable valve may be used, including but not limited to a wax valve.

The reservoir 532 may generally be implemented using any size and shape, and may contain one or more reagents including solids and/or fluids which may interact with fluid entering and/or exiting the features. The reservoir 532 may be implemented as the device 405 of FIG. 4 or the device 205 of FIG. 2. The reservoir 532 may be configured to contain a density medium and receive a mixture containing the sample and coated particles. The substrate 510 may spin, for example in a direction indicated by the arrow in FIG. 5 (or in the opposite direction in other examples), and the spinning of the substrate may generate a centrifugal force which may provide the sedimentation forces described above to move unbound beads and/or agglutinate toward a detection area 540.

The detection area 540 may be a channel or chamber, or a location within a particular feature, such as an end of the reservoir 532 in FIG. 5, and may vary in configuration in accordance with the detection technique employed. The detection area 530 may generally be configured to allow for detection of a signal emitted by labels on coated particles on unbound particles and/or aggregates.

Figure 6:
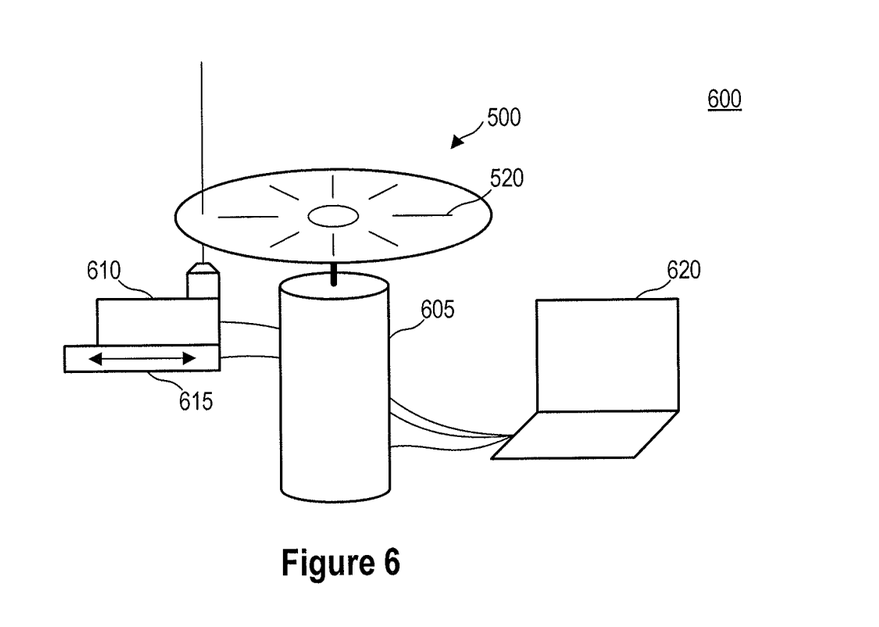
FIG. 6 is a schematic illustration of a system according to an embodiment of the present invention.

FIG. 6 is a schematic illustration of a system according to an embodiment of the present invention. The system 600 may include the device 500 of FIG. 5 with one or more assay areas 520. A motor 605 may be coupled to the device 500 and configured to spin the device 500, generating centrifugal forces. A detection module 610 may be positioned to detect signal from labels in a detection region of the assay area 520, as will be described further below. An actuator 615 may be coupled to the detection module 610 and configured to move the detection module along the detection region in some examples. A processing device 620, e.g. a computer, controller, or the like, may be coupled to the motor 605, the detection module 610, and/or the actuator 615 and may provide control signals to those components. The processing device 620 may further receive electronic signals from the detection module 610 corresponding to the label signals received by the detection module 610. The processing device 620 may allow for automated control of the motor 605 and detection module 610 such that multiple parallel assays on the device 500 may be automated. All or selected components shown in FIG. 6 may be housed in a common housing in some examples. Microfluidic disks, which may be disposable, may be placed on the motor 605 and removed, such that multiple disks may be analyzed by the system 600.

The motor 605 may be implemented using a centrifugation and/or stepper motor. The motor 605 may be positioned relative to the detection module 610 such that, when the device 500 is situated on the motor 605, the disk is positioned such that a detection region of the assay area 520 is exposed to the detection module 610.

The detection module 610 may include a detector suitable for detecting signal from labels on the coated particles described herein. The detector may include, for example, a laser and optics suitable for optical detection of fluorescence from fluorescent labels. The detection module may include one or more photomultiplier tubes. In other examples, other detectors, such as electronic detectors, CCD cameras, or other cameras (e.g. cell phone cameras), may be used. The actuator 615 may move the detector in some examples where signal may be detected from a variety of locations of the microfluidic device 500, as will be described further below.

The processing device 620 may include one or more processing units, such as one or more processors. In some examples, the processing device 620 may include a controller, logic circuitry, and/or software for performing functionalities described herein. The processing device 620 may be coupled to one or more memories, input devices, and/or output devices including, but not limited to, disk drives, keyboards, mice, and displays. The processing device may provide control signals to the motor 605 to rotate the device 500 at selected speeds for selected times, as has been described above. The processing device may provide control signals to the detection module 610, including one or more detectors and/or actuators, to detect signals from the labels and/or move the detector to particular locations. The processing device may develop these control signals in accordance with input from an operator and/or in accordance with software including instructions encoded in one or more memories, where the instructions, when executed by one or more processing units, may cause the processing device to output a predetermined sequence of control signals. The processing device 620 may receive electronic signals from the detection module 610 indicative of the detected signal from labels. The processing device 620 may detect an analyte of interest and/or calculate a quantity of a target analyte in a fluid sample based on the signals received from the detection module 610, as has been described above. Accordingly, the processing device 620 may perform calculations. The calculations may be performed in accordance with software including one or more executable instructions stored on a memory causing the processing device to perform the calculations. Results may be stored in memory, communicated over a network, and/or displayed. It is to be understood that the configuration of the processing device 620 and related components is quite flexible, and any of a variety of computing systems may be used including server systems, desktops, laptops, controllers, and the like.

From the foregoing it will be appreciated that, although specific embodiments of the invention have been described herein for purposes of illustration, various modifications may be made without deviating from the spirit and scope of the invention.

What is claimed is:

1. A method comprising:
   layering a mixture on a density medium, wherein the mixture includes a sample and a first population of coated beads having a first density, wherein the first population of coated beads include affinity reagents for an analyte of interest, wherein the first population of coated beads is configured to form aggregates with the analyte interest when present, wherein the density medium has a minimum density greater than the first density;
   subjecting the mixture to sedimentation forces such that the aggregates, if formed, travel through the density medium; and
   detecting a presence of the aggregates in a detection area.

2. The method of claim 1, the mixture further comprising a second population of coated beads having a second density, and wherein the minimum density of the density medium is less than the second density.

3. The method of claim 2 wherein the first population of coated beads further include a detection label.

4. The method of claim 2, wherein the first population of coated beads are configured to remain at an interface between the sample and the density medium responsive to the sedimentation forces if the first population of coated beads are not bound in the aggregates.

5. The method of claim 2, wherein the first population of coated beads are configured to form the aggregates with the analyte of interest and the second population of coated beads, such that the detection label travels to the detection area responsive to the sedimentation forces.

6. The method of claim 1, wherein the sedimentation forces are generated by gravity.

7. The method of claim 1, wherein the sedimentation forces are generated by centrifugal force.

8. The method of claim 1, wherein said subjecting the mixture to sedimentation forces comprises subjecting the mixture to sedimentation forces for a fixed time.

9. The method of claim 8, wherein the fixed time is selected such that the aggregates of the coated beads and analyte of interest are configured to travel to the detection area within the fixed time and unbound coated beads do not reach the detection area within the fixed time.

10. The method of claim 1, further comprising preparing the mixture including mixing the sample with the coated beads.

11. The method of claim 1, wherein said layering a mixture on a density medium comprises providing the mixture on the density medium in a vial.

12. The method of claim 1, wherein said layering a mixture on a density medium comprises inputting the mixture to a reservoir of a microfluidic device containing the density medium.

13. The method of claim 1, wherein said detecting comprises quantifying an amount of the analyte of interest.

14. The method of claim 1, wherein the analyte of interest comprises a protein.

\* \* \* \* \*